(12) United States Patent
Chartrand et al.

(10) Patent No.: US 6,342,354 B1
(45) Date of Patent: Jan. 29, 2002

(54) METHOD TO MAP AND ISOLATE REGIONS OF CHROMOSOMES THAT INTERACT OR ASSOCIATE FUNCTIONALLY WITHIN OR BETWEEN CHROMOSOMES IN VIVO

(75) Inventors: Pierre Chartrand, Laval; Graham Dellaire, Montréal, both of (CA)

(73) Assignees: Université de Montréal; Centre Hospitalier de l'Universitéde Montréal (CHUM), both of Montréal (CA)

( * ) Notice: Subject to any disclaimer, the term of this patent is extended or adjusted under 35 U.S.C. 154(b) by 0 days.

(21) Appl. No.: 09/453,221

(22) Filed: Dec. 3, 1999

Related U.S. Application Data

(63) Continuation of application No. PCT/CA98/00532, filed on May 29, 1998.

(30) Foreign Application Priority Data

Jun. 4, 1997 (CA) .............................................. 2205081

(51) Int. Cl.$^7$ .......................... C12Q 1/68; C12N 15/00; C12N 5/00; C12N 13/00; C12P 19/34; C07H 21/04; G01N 33/564

(52) U.S. Cl. ........................ 435/6; 435/320.1; 435/325; 435/91.1; 435/91.2; 435/69.1; 435/173.6; 435/455; 536/23.1; 536/24.33; 536/24.3; 436/504

(58) Field of Search .......................... 435/6, 69.1, 91.1, 435/91.2, 320.1, 325, 455, 173.6; 536/23.1, 22.1, 24.3; 436/504

(56) References Cited

PUBLICATIONS

Adair, G.M. et al., (1989) "Targeted homologous recombination at the endogenous adenine phosphoribosyltransferase locus in Chinese hamster cells" *Proc. Natl. Acad. Sci.* 86: 4574–4578.

Belmaaza, A. et al., (1994) "One–sided invasion events in homologous recombination at double–strand breaks" *Mut. Res.* 314: 199–208.

Belmaaza, A. et al., (1990) "Genetic exchange between endogenous and exogenous LINE–1 repetitive elements in mouse cells" *Nucl. Acids Res.* 18: 6385–6391.

Cook, P.R. (1995) "A chrommomeric model for nuclear and chromosome structure" *J. Cell Sci.* 108: 2927–2935.

Cremer, T. et al., (1993) "Bole of Chromosome Territories in the Functional Compartmentalization of the Cell Nucleus" *Cold Spring Harbor Symp. Quant. Biol.* 58: 777–792.

Ausubel, F. et al. (1996) *Current Protocols in Molecular Biology* 2: 9.1.4–9.1.9.

Ellis, J. et al., (1989) "Gene Targeting with retroviral Vectors: Recombination by Gene Conversion into Regions of Nonhomology" *mol. Cell Biol.* 9: 1621–1627.

Folger, K. R. et al., (1982) "Patterns of Integration of DNA Microinjected into Cultured Mammalian Cells: Evidence for Homologous Recombination Between Injected Plasmid DNA Molecules" *Mol. Cell. Biol.* 2: 1372–1387.

Huang, L. C. et al., (1996) "Sensitivity and selectivity of the DNA damage sensor responsible for activating p53–dependent $G_1$ arrest" *Proc. Natl. Acad. Sci. USA* 93: 4827–4832.

Jackson, D.A. (1995) "Nuclear organization: uniting replication foci, chromatin domains and chromosome structure" *Bioessays* 17: 587–591.

Lemieux, N. et al., (1994) "A simple method for simultaneous R–or G–banding and fluorescence in situ hybridization of small single–copy genes" *Cytogenet. Cell Genet* 59: 311–312.

Renzing, J. et al. (1995) "p53–dependent growth arrest following calcium phosphate–mediated transfection of murine fibroblasts" *Oncogene* 10: 1865–1868.

Richard, M. et al. (1994) "Intergration of a Vector Containing a Repetitive LINE–1 Element in the Human Genome" *Mol. Cell. Biol.* 14: 6689–6695.

Rouet, P. et al., (1994) "Introduction of Double–Strand Breaks into the Genome of Mouse Cells by Expression of a Rare–Cutting Endonuclease" *Mol. Cell. Biol.* 14: 8096–8106.

Spector, D. L. et al., (1993) "Dynamics of Transcription and Pre–mRNA Splicing within the Mammalian Cell Nucleus" *Cold Spring Harbor Symp. Quant. Biol.* 58: 799–805.

Trask, B.J., (1991) "Fluorescene in situ hybridization: applications in cytogenetics and gene mapping" *Trend. Genet.* 7: 149–154.

Wolffe, A. (1998) *Chromatin: Structure and Function*, Third Edition.

Berinstein et al. Gene Replacement with One–sided homologous recombination. Molecular and Celluar Biology, vol. 12, No. 1, pp. 360–367.*

Aratani et al. End extension repair of introduced targeting vectors mediated by homologous recombination in mammalian cells Nucleic acids Research, vol. 20, No. 18, pp. 4795–4801, Sep. 1992.*

(List continued on next page.)

*Primary Examiner*—Stephanie W. Zitomer
*Assistant Examiner*—Cynthia B Wilder
(74) *Attorney, Agent, or Firm*—Crowell & Moring LLP

(57) ABSTRACT

The present invention relates to a linear DNA vector and to a method for identifying chromosomal regions having a physical proximity within a living cell, and/or for locating in chromosomes of a living cell a DNA double strand break having a physical proximity with a known non-repetitive DNA sequence. The linear DNA vector has a first end which comprises a nucleotide sequence capable of homologous recombination to a first region of a cell chromosome which comprises a known non-repetitive DNA sequence. The linear DNA vector also has a second end which comprises a nucleotide sequence non-homologous to the chromosomes of the cell and being capable of illegitimate integration with a second region of a chromosome in physical proximity to the first chromosomal region.

21 Claims, 6 Drawing Sheets

OTHER PUBLICATIONS

Berinstein et al. Gene Replacement with OneOsided homologous recombination. Molecular and Celluar biology, vol. 12, No. 1, pp. 360–367, Sep. 1992.*

Richard et al. Integration of a vector containing a repetitive LINE–1 element in the human genome. Molecular and Cellular Biology, vol. 14, No. 10, pp. 6689–6695, Oct. 1994.*

Ellis et al. Gene targeting with retroviral vectors: Recombination by gene conversion into regions of nonhomology. Molecular and Cellular Biology. vol. 9, No. 4, pp. 1621–1627, Apr. 1989.* levy et al. Application of chromosomal in situ hybridization. Gene Probes, Apractical Approach. IRL press, New York pp. 211–225, Feb. 1996.*

Trask, Fluorescence in situ hybridization: Applications in cytogenetics and gene mapping. Trends Genetics. Vol. 7, pp. 149–154, Dec. 1991.*

Rouet et al. Introduction of Double strand breaks into the genome of mouse cells by expression of a rare cutting endonuclease. Molecular and cellular biology vol. 14, No. 12, pp. 8096–8106, Dec. 1994.*

Belmaaza et al. Genetic exchange between endogenous and exogenous LINE–1 repetitive elements in mouse cells. Nucleic Acids Research. Vol. 18, No. 21 pp. 6385–6391, Oct. 1990.*

Lemieux et al. A simple method for simultaneous R–or G–banding and fluorescence in situ hybridization of small single–copy genes. Cytogenet Cell Genet. Volu. 59, pp. 311–312, Dec. 1992.*

Dickinson et al. An atypcial homedomain in SATB1 promotes specific recognition of the key structural element in a marix attachment region. The Journal of Biological Chemistry. vol. 272, No. 17, pp. 11463–11470, Apr. 1997.*

Kahl, G. Dictionary of Gene Technology, VCH Publisher, Inc, New York, NY (USA), pp. 235–237, Oct 1994.*

* cited by examiner

METHOD TO MAP AND ISOLATE REGIONS OF CHROMOSOMES THAT INTERACT OR ASSOCIATE FUNCTIONALLY WITHIN OR BETWEEN CHROMOSOMES IN VIVO

RELATED APPLICATION

This application is a continuation of PCT/CA98/00532 filed May 29, 1998 designating the United States and claiming priority of Canadian Patent Application Number 2,205,081 filed Jun. 4, 1997.

BACKGROUND OF THE INVENTION (a) Field of the Invention

The invention relates to a method for mapping and isolating regions of chromosomes that interact together or associate functionally in vivo. The method of the present invention is also referred to as recombination access mapping (RAM).

(b) Description of Prior Art

Currently in the field of molecular biology, it is becoming quite evident that gene regulation occurs through a complex network of processes. Transcription, replication and recombination of DNA must occur in a timely and appropriate manner or the outcome may be disastrous. Extreme control over these processes is required during development and differentiation of tissues in multicellular organisms. In contrast, disorder of these processes occurs during oncogenesis. Cancer cells often exhibit aberrant expression of genes as well as general genomic instability, a hallmark of which is an increase in recombination rates.

Activation or repression of gene expression by transcription factors or repressors respectively has been studied in great detail both in vitro and in vivo. Changes in chromatin structure are intimately linked to the activation or inactivation of a gene and can affect the replication or recombination of DNA. Mostly in vitro studies and limited in vivo data has been used to determine such changes in chromatin as they relate to DNA transcription, replication and recombination. From this data it is apparent that chromatin is organized in DNA loop domains that are organized through interaction with a nuclear protein matrix. These domains average in size from 60–100 kb and are assumed to be flanked by matrix attachment regions (MARS). MARS have been associated with functional domains of transcription and replication. Indirect methods such as DnaseI sensitivity and DNA cleavage assays involving topoisomerase inhibitors, have provided further evidence of higher order chromatin domains which may correspond to single loops (60–100 kb) and loop arrays (300 kb). Functional chromatin domains seem to exist for transcription and replication (reviewed by in Jackson, D. A., *Bioessays* 17:587–591, 1995). Strong evidence exists which suggests chromatin structure also plays a role in recombination as in VDJ recombination, formation and repair of double strand breaks in irradiated cells, and during meiosis; differences in meiotic recombination between imprinted domains.

Therefore, the central question is raised as to the interaction between chromatin domains and their accessibility to biological molecules are involved in gene regulation. Many studies of chromatin focus on in vitro data at the nucleosomal level (Wolffe, A. Chromatin: Structure and Function, Second Ed. *Academic Press Inc.* San Diego 1995). Unfortunately, it is most likely that large scale changes in chromatin packaging beyond the nucleosomal level are primarily responsible for the maintenance of certain chromatin states, such as early or late replication and hetero vs. euchromatin. Very few techniques exist to analyze DNA interaction in vivo in a global fashion over the entire genome.

Ectopic gene targeting is an alternative outcome of the gene targeting process in which a targeting vector acquires sequences from a genomic target but proceeds to integrate elsewhere in the genome. More specifically, ectopic gene targeting is a process by which an extra chromosomal molecule (recipient) obtains DNA sequence from a target locus via one-end invasion and gene conversion followed by release of the recipient molecule and integration, complete with the newly acquired sequence from the target locus, Aelsewhere in the genome. Such events were first observed in gene targeting experiments involving the adenine phosphoribosyl transferase (APRT) locus in CHO cells (Adair, G. M., et al., *Proc. Natl. Acad. Sci. USA* 86:4574–4578, 1989) and in experiments involving retroviral transfection of rat cells (Ellis, J. et al., *Mol. Cell. Biol.* 9:1621–1627, 1989). Consequently, a model has been proposed for the mechanism of ectopic gene targeting (Belmaaza, A., et al., *Nucl. Acids Res.* 18:6385–6391, 1990; and Belmaaza, A. et al., *Mut. Res.* 314:199–208, 1994). Instances of ectopic gene targeting and/or ectopic gene conversion have been seen in Drosophila (roo element, p and hobo elements), plants, yeast (between dispersed repeated genes or Ty 1 repeat elements), fungi (in Ustilago maydis, chickens (Ig rearrangement)), rabbit (generation of antibody repertoire), mice (germline ectopic gene conversion in spermatids, gene conversion between Line-1 elements, and humans (gene conversion between Line-1 elements and pseudo autosomal region on X and Y chromosome).

Although the phenomenon of ectopic gene targeting is well documented, the question of where the recipient molecule integrates, with respect to the target locus, has not been determined. It is apparent from Southern analysis that the recipient integrates in most cases at a distinct site from the target but Southern analysis does not permit the determination of the relative position of the ectopic sites with regard to the target locus.

It would be highly desirable to be provided with a method allowing the identification of interactions between chromatin domains within or between chromosomes which may be involved in gene regulation. With such a method, the functional organization of the genome could be mapped. The understanding the three-dimensional (3-D) in vivo interactions between chromosome could help to better understand complex gene regulation during cancer or other disease states.

SUMMARY OF THE INVENTION

One aim of the present invention is to provide a method allowing to define functional organization of chromatin in vivo with respect to interchromosomal and interchromatin domain interactions involved in gene regulation, including but not limited to replication, transcription and recombination.

Another aim of the present invention is to provide a method allowing to mark domains of chromatin that interact functionally in vivo with a given gene locus for the purpose of cloning such domains or their visualization in 3-D using confocal fluorescent microscopy.

Another aim of the present invention is to provide a method allowing to define points of interaction between chromosomes involved in translocation or ectopic gene conversion within or between chromosomes.

Another aim of the present invention is to provide a method allowing to define chromatin domain interactions between chromosomes involved in epigenetic phenomenon such as imprinting, position effect variegation and transvection.

Another aim of the present invention is to provide a method allowing to produce diagnostic ectopic gene targeting distribution profiles, such as fingerprints, for a given gene locus.

Another aim of the present invention is to provide a method allowing to determine changes in genomic organization associated with various disease states as a means of monitoring disease progression or onset.

Another aim of the present invention is to provide a method allowing to study developmental changes in multicellular organisms such as during tissue development.

Another aim of the present invention is to provide a method allowing for the placement of DNA elements or recognition sites for enzymes for the purpose of chromosomal engineering.

Another aim of the present invention is to provide a means for mapping the distribution of double strand breaks in DNA, which are natural breaks or induced by any means, over a given region of a chromosome with respect to a chromosomal DNA sequence to be studied, which in turn allows for the definition, characterization and cloning of structural and/or functional genomic domain(s) containing the chromosomal sequence being studied.

A further aim of the present invention is to provide a method allowing to assess the affects of a given drug or chemical on genomic organization and stability such as for defining oncogenic potential of a substance.

A still further aim of the present invention is to provide a method allowing to define at what time in a cell cycle chromatin domains associate functionally.

In accordance with the present invention there is provided a method hereinafter referred to as recombination access mapping (RAM), that enables the elucidation of DNA interaction between domains of chromatin within the genome, in vivo.

In accordance with the present invention, there is provided a method for identifying chromosomal regions having a physical proximity within a living cell, comprising the steps of:

a) providing a linear DNA vector having a first end and a second end, the first end of the vector comprising a nucleotide sequence homologous to a first region of a chromosome and being capable of homologous recombination thereto, the first chromosomal region comprising a known non-repetitive DNA sequence; the second end of the vector comprising a nucleotide sequence non-homologous to the chromosomes of the cell and being capable of illegitimate integration with a second region of a chromosome in physical proximity to the first chromosomal region;

b) introducing the DNA vector into the cell;

c) allowing the first end of the vector to recombine with the first chromosomal region, and the second end to illegitimately integrate with the second chromosomal region; and d) detecting the homologous recombination event and the second chromosomal region whereupon the second end of the vector illegitimately integrated, thereby identifying chromosomal regions having a physical proximity within said living cell.

In accordance with another embodiment of the present invention, there is provided a method for locating in chromosomes of a living cell a DNA double strand break having a physical proximity with a known non-repetitive DNA sequence, comprising the steps of:

a) providing a linear DNA vector having a first end and a second end, the first end of the vector comprising a nucleotide sequence homologous to a first region of a chromosome comprising a known non-repetitive DNA sequence and being capable of homologous recombination thereto, the second end of the vector comprising a nucleotide sequence non-homologous to the chromosomes of the cell and being capable of illegitimate integration into a DNA double strand break of a chromosome in physical proximity to the first chromosomal region;

b) introducing the DNA vector into the cell;

c) allowing the first end of said vector to recombine with the first chromosomal region and the second end to illegitimately integrate into the DNA double strand break; and d) detecting the homologous recombination event and the DNA double strand break whereupon the second end of the vector illegitimately integrated, thereby locating the DNA double strand break having a physical proximity with said known non-repetitive DNA sequence.

In accordance with the present invention, there is also provided a linear DNA vector having a first end and a second end. The first end of the vector comprises a nucleotide sequence capable of homologous recombination to a first region of a cell chromosome comprising a known non-repetitive DNA sequence. The second end of the vector comprises a nucleotide sequence non-homologous to the chromosomes of the cell and is capable of illegitimate integration with a second region of a chromosome, the second chromosomal region being in physical proximity to the first chromosomal region.

The DNA vector of the invention can be used for identifying chromosomal regions having a physical proximity within a living cell, and/or for locating in chromosomes of a living cell a DNA double strand break having a physical proximity with a known non-repetitive DNA sequence.

Preferably, the DNA vector of the invention further comprises, at each one of its ends, at least one detection element selected from the group consisting of a tag, a label, a signal, a polymerase chain reaction (PCR) primer sequence, a reporter gene and a portion of a reporter gene.

More preferably, the DNA vector comprises at least one signal selected from the group consisting of fluorescence in situ hybridization signals (FISH), radioactive in situ hybridization signals, confocal microscopy in situ hybridization signals and electron microscopy in situ hybridization signals. The signal(s) allows for detection of in situ hybridization of the DNA vector.

According to the present invention, the first region of a chromosome may be modified to introduce a first part of a reporter gene, and wherein the linear DNA vector comprises a second part of the reporter gene, such that recombination of the first end of the vector with the first chromosomal region, and illegitimate integration of the second end with the second chromosomal region allows the reporter gene to be functional. The reporter gene may be a selection gene selected from the group consisting of neomycin, puromycin, hygromycin, and herpes simplex thymidine kinase.

The first end of the linear DNA vector according to the invention may have a nucleotide sequence of at least 300 bp in length, preferably of at least 500 pb in length, and more preferably of about 700 pb in length. The second end of the vector is at least 1 Kb in length, preferably of about 10 Kb in length.

The method of the present invention as described above may preferably be used to characterize or identify functional or structural sequence elements such as origins of replication, matrix attachment sites, transcription factor binding sites, imprinting centers or insulator elements. Of course, the double strand breaks may be have been formed in vivo or in vitro.

DETAILED DESCRIPTION OF THE INVENTION

Figure 1A:
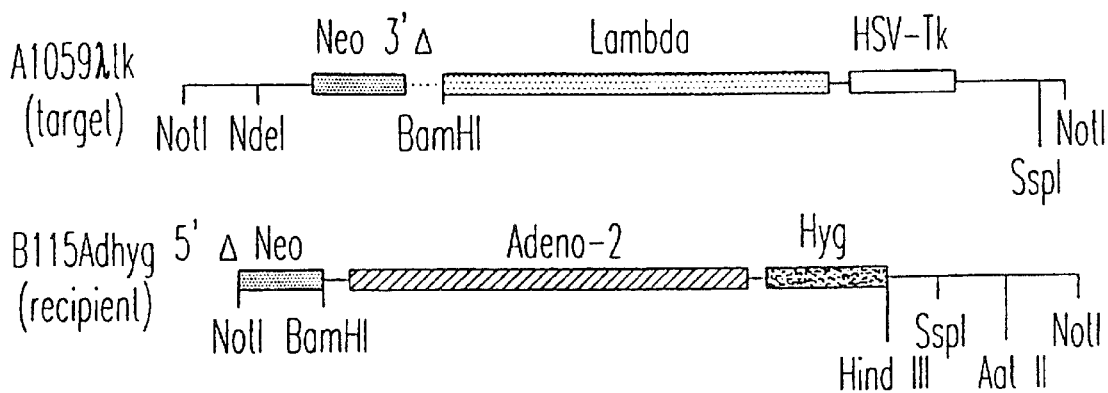
FIGS. 1A and 1B illustrate a preferred embodiment of RAM method in accordance with the present invention.

In accordance with the present invention, there is provided a Recombination Access Mapping (RAM) method. Preferably, two vectors which can recombine to produce a functional gene such as neo+ via a one-end invasion mechanism of recombination (Adair, G. M., et al., *Proc. Natl. Acad. Sci. USA* 86:4574–4578, 1989; Ellis, J., et al., *Mol. Cell. Biol.* 9:1621–1627, 1989; Belmaaza, A., et al., *Nucl. Acids Res.* 18:6385–6391, 1990; and Belmaaza, A. et al., *Mut. Res.* 314:199–208, 1994) are used in the method of the present invention. Cells are transfected with a "target" vector. Clones containing the "target" vector are then transfected with a "recipient" vector. Ectopic gene targeting events are selected for example by G418 resistance. The distribution of ectopic events in relation to the target locus may be determined using two-color fluorescent in situ hybridization (FISH). Integration of the recipient may occur in close proximity to the target locus (close events: less than 2–3 Mb from the target) or in other chromosomes other than the target chromosome (far events). The distribution of ectopic integration is distinct for each locus and provides a "fingerprint" of chromatin domain interactions for a particular gene which are distinct for a given tissue, developmental stage or disease state. Interphase FISH analysis of far ectopic gene targeting events indicates that the chromatin domains containing each respective vector can associate even though the recipient has integrated in distinct chromosome from the target chromosome.

Therefore, such domains may be identified and cloned. Cloned domains may contain important enhancers or silencers and/or other regulatory elements of gene expression. They may also contain origins of replication and/or regulatory DNA elements involved in the replication of DNA. These domains correspond to DNA elements which may inturn be used to find DNA binding proteins responsible for gene regulation and the functional structure of chromatin.

Fluorescent in situ hybridization (FISH) analysis, which can be used to identify the genomic location of distinct DNA sequences with a general resolution of 100 Kb at interphase and 2–3 Mb at metaphase (Trask, B. J., *Trend.Genet.* 7:149–154, 1991), provides a unique tool for analysis of DNA sequences with respect to their chromosomal positions and with respect to each other.

A method for studying ectopic gene targeting that uses two vectors, a "target" and a "recipient" vector which can recombine to produce a functional gene (neo+) via the one-end invasion mechanism of recombination has been developed. A murine fibroblast cell line (LTA) was transfected with the "target" vector. Three distinct clones containing the "target" vector integrated in their genome were then transfected with the "recipient" vector. Ectopic gene targeting events, which are characterized by the acquisition of sequences from the target by the recipient vector and then its integration in the genome, were selected preferably by G418 resistance. The distribution of ectopic gene targeting events in relation to the target locus was determined using two-color FISH. The results indicate that the distribution of ectopic gene targeting events is bimodal. Ectopic integration of the recipient vector occurred either in close proximity to the target locus (<2–3 Mb) or in altogether different chromosomes from the target chromosome. In contrast, illegitimate integration showed no bias for any single chromosome or chromosomal location at megabase resolution. A corollary to these observations is that both inter and intrachromosomal DNA interactions appear to occur during ectopic gene targeting. Therefore, the method could be used to determine which chromosomal domains within the genome are accessible to a given genetic locus.

The method of the present invention will be referred to as Recombination Access Mapping or RAM. In its most basic form, a vector comprising only minimal homology (about 300 bp) to a target locus in the genome, which may be a native DNA locus or exogenous sequences and whose location or identity may or may not be known, is utilized. This minimal recipient vector can undergo ectopic gene targeting at the target locus and upon integration, the position of the recipient vector may be mapped by inverse PCR or other oligo based technologies. Selection of ectopic gene targeting events would occur by PCR in which a band is only produced upon recombination of the target locus and the recipient vector. By this means, rapid large scale "RAM fishing" may be effected using minimal sized fragments of DNA to map in vivo, 3-D chromatin interactions over the entire genome.

Figure 1B:
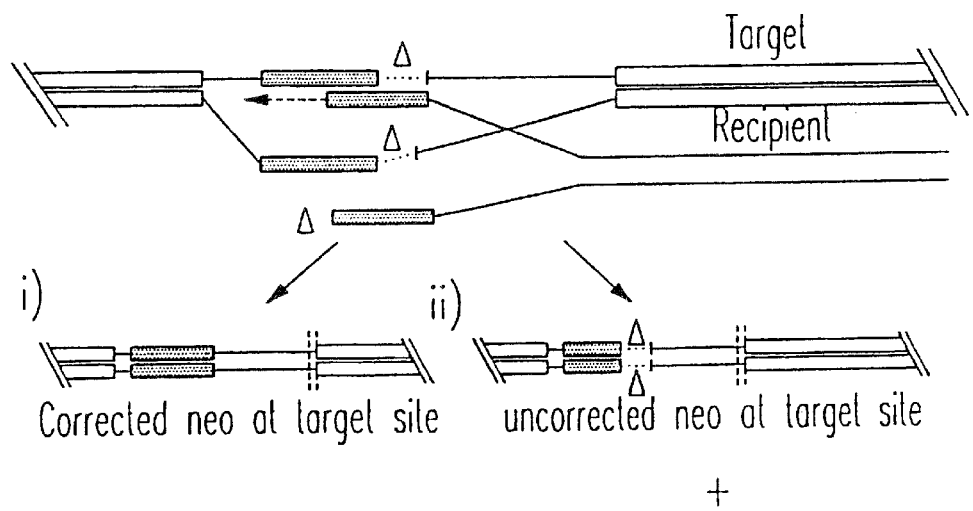

FIG. 1A illustrates two plasmid based vectors used in the RAM method in accordance with a preferred embodiment of the invention. The vectors are depicted in linear form after digestion via Not I prior to transfection. The vector A1059λtk (target) contains a 3' truncated neo cassette. Vector B115Adhyg (recipient) contains a 5' truncated neo cassette. Both vectors contain selection markers for illegitimate integration (HSV-tk and Hyg, respectively) and specific DNA for detection via FISH analysis (lambda DNA and adenovirus-2 DNA, respectively). FIG. 1b illustrates the mechanism of ectopic gene targeting leading to reconstruction of a functional neo gene between an integrated copy of the target vector and an extra chromosomal recipient molecule. A simplified version of the vectors from panel A are depicted for clarity. One-end invasion of the of the target locus by the homologous 3' end of the recipient molecule leads to the formation of a D-loop. The invading 3' end of the recipient primes DNA sythesis leading to gene conversion and extension of the D-loop. Resolution by nicking of the D loop results in non-crossover and crossover products, the later involving integration within the target locus (i). Alternately, resolution can occur via unwinding of the newly sythesized strand and release of the recipient molecule or its displacement due to branch migration. In the case of a non-crossover event, the recipient molecule may integrate illegitimately in a different locus leaving the target locus unchanged (ii). Integration of the recipient molecule after gene conversion, elsewhere than within the target locus, is termed ectopic gene targeting. Illegitimate junctions are depicted via double, horizontal dashed lines where recipient DNA is joined to chromosomal DNA in the absence of homology.

FIG. 2 illustrates southern analysis of mother clones A1, A6 and A14 and selected daughter clones. Genomic DNA was isolated and digested before electrophoresis and capillary transfer to nylon membranes as described in materials and methods. DNA was digested with either BamHI alone (A, B and C) or in combination with NdeI (see D) and blots were probed with a neo probe that lacked the promoter sequences (Eag I/HincII fragment of pMCIneopA). Hind III digested lambda DNA was used as a marker of molecular weight and is shown in lane λ. Lane A contains the digestion profiles of mother clone A1 and five daughter clones. Two specific bands appear for the mother clone A1 (see A, lane A1 and E, A1). The two bands indicate that two target vectors are arranged head to tail in which the 5.6 kb band represents an intervector band and the 8 kb band spans the junction of one vector with genomic sequences (E, A1).These bands are maintained in 4 daughter clones (A1.2, A1.3, A1.5 and A1.9) indicating the target locus has remained intact in these clones. A1.12 is an exception in which the junction band has increased in size to approximately 8.2 kb suggesting reconstruction of the full neo gene. Digestion with NdeI in combination with BamHI should produce a 1.1 kb band for the target locus or a 1.3 kb band for a corrected neo gene (D). In the case of A1.2 and A1.5 the target locus remains uncorrected (i.e. maintenance of 1.1 bk band) while the recipient is corrected producing a 1.3 kb band. Clone A1.12, on the other hand, exhibits only a 1.3 kb band indicating that the target locus has been corrected. Such a pattern is indicative of a crossover event in A1.12 which has replaced downstream sequences from the neo gene of one vector (including the neo gene and lambda sequences of both target vectors) with sequences from the recipient (E, A1.12). In B the digestion profiles of A6 and five daughter clones are shown. Lane A6 shows a single target band of 5.0 kb which is maintained in all five daughter clones (lane A6.2 through to A6.6) and represents a single integration of the target locus (E, A6). In C the digestion profiles of A14 and five daughter clones are shown. A single 3.8 kb band appears for A14 which indicates a single integration of the target locus in these clones (E, A14). This band is maintained in all daughter clones except for A14.4 in which the target band is shifted slightly to approximately 4.0 kb (C, A14.4). Again this would indicate that the target locus had been corrected. Indeed, double digestion with NdeI and BamHI gives the same profile as seen for A1.12. All other bands represent integrations of the recipient vector.

Figure 3:
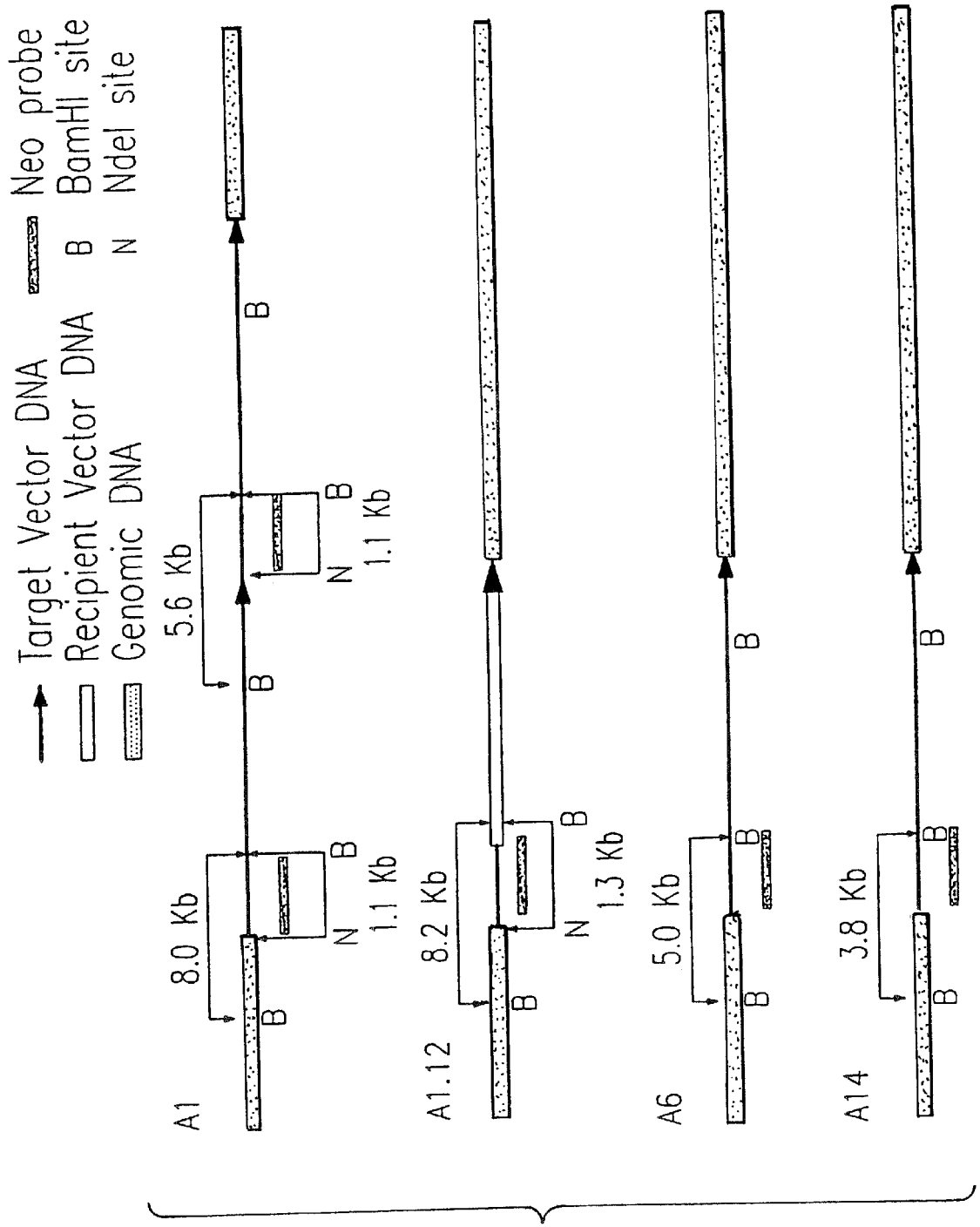
FIG. 3 illustrates the arrangement of the vectors sequences and their restriction enzyme sites used with a RAM method in accordance with one embodiment of the present invention to obtained the clones of FIG. 2.

FIG. 3 illustrates an arrangement of vector sequences in the genome, as well as restriction enzyme sites in accordance with the method of the present invention.

FIG. 4 illustrates a FISH analysis of mother clones A1, A6 and A14 and selected daughter clones. Cell cultures were prepared for in situ hybridization and FISH analysis was carried out. DNA was counterstained with either propidium iodine (red, A, F and I) or DAPI (blue, B–E, G, H, J and K). Target sequences appear as green signals on a blue background or yellow on a red background. Recipient sequences appear as red signals against a blue background. Frame A shows a full complement of chromosomes from the mother clone A1 in which two copies of the target vector have been integrated into a dicentric chromosome between two centromeres (white arrow). Daughter clones A1.2 (B) and A1.5 (C) have integrated the recipient (small arrow) in close proximity to the target locus (large white arrow). Both the green and red signals can be seen separately rather than as a single white or yellow dot, suggesting the recipient and target sequences are more than 100 kb but not more than 2–3 Mb apart (Trask, B. J., Trend.Genet. 7:149–154, 1991). In clone A1.9 (D) the recipient sequences have integrated in the midarm of an acrocentric chromosome (small arrow) while the target locus has remained intact in the dicentric chromosome (large arrow). Clone A1.12 (E) shows a crossover event in which the target sequences have been completely replaced by the recipient sequences at the target locus (white arrow) Mother clone A6 is depicted in frame F in which a single target vector has integrated into small satellite arms of an acrocentric chromosome (white arrow). In both clone A6.2 and A6.3 the recipient sequences have integrated in the midarm of acrocentric chromosomes (see small arrows in G and H, respectively) leaving the target locus intact in the original acrocentric chromosome (large arrows). Frame I shows the single integration of a target vector in the mid arm of a metacentric chromosome in mother clone A14 (white arrow). The recipient sequences (small arrow) have integrated into the same metacentric chromosome within 2–3 Mb of the target locus (large arrow) in clone A14.4 (J). This is interesting as Southern analysis indicates a crossover event which should have resulted in an intermediate white signal (juxtaposition of recipient and target DNA) or loss all together of the green signal (i.e. target locus) as in A1.12 (E). Thus this clone may represent a rare event in which a crossover occured but the recipient was still able to integrate ectopically. Such a "broken arrow" suggests the commitment of both ends of the recipient molecule at the time of the recombination event rather than sequential participation of each end in recombination. Clone A14.6 is also shown in frame K, in which recipient sequences have integrated into the telomere of an acrocentric chromosome (small arrow) and the metacentric chromosome containing the target vector (large arrows) has been duplicated, most likely by a non disjunction event.

Figure 5:
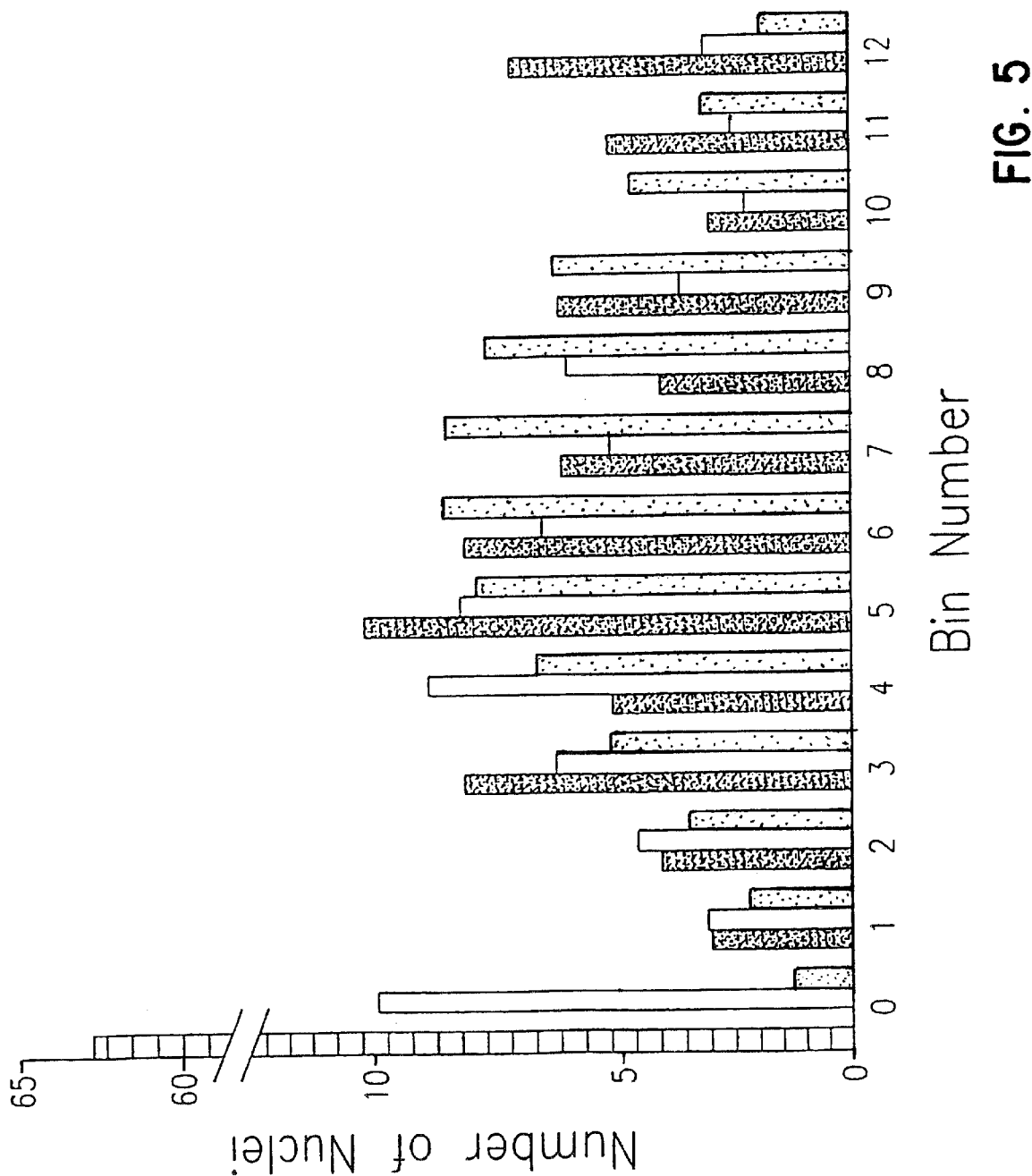
FIG. 5 illustrates a histogram of inter signal distances determined for target and recipient FISH signals in interphase nuclei.

FIG. 5 illustrates a histogram of the distribution of inter signal distances determined for target (green) and recipient (red) FISH signals in interphase nuclei. Photographic slides of nuclei were projected at distance of 3 m onto a screen and distances between red and green signals were measured in cm. The inter signal distances were pooled in bins of 0 to 12 cm (average diameter of an interphase nuclei) in 1 cm intervals. FIG. 5 depicts a histogram of the number of nuclei in each bin for random, unlinked sequences (grey bar; n=69; data from a two independent pools of ~220 clones), linked sequences (horizontal striped bar; n=63; from pooled data from 3 independent clones) and for far ectopic events (white bar; n=247; pooled data from 9 independent clones). Bin 0 represents co-localization or near co-localization of red and green signals. All values have been normalized for 63 nuclei. Black bars represent the normal distribution expected from the mean (6.37 cm) and standard deviation (3.27 cm) of the observed andom, unlinked inter signal distances. The far ectopic events follow a normal distribution for bins 1–12 but the observed number of co-localizations seen (i.e. ~10 nuclei in bin 0) deviates significantly from the expected number (~1) with a p value of less than 0.0001. (note: although data were pooled for several clones to increase the total number of nuclei observed, no significant deviations were seen between independent clones with regard to the distribution of inter signal distances).

Figure 6:
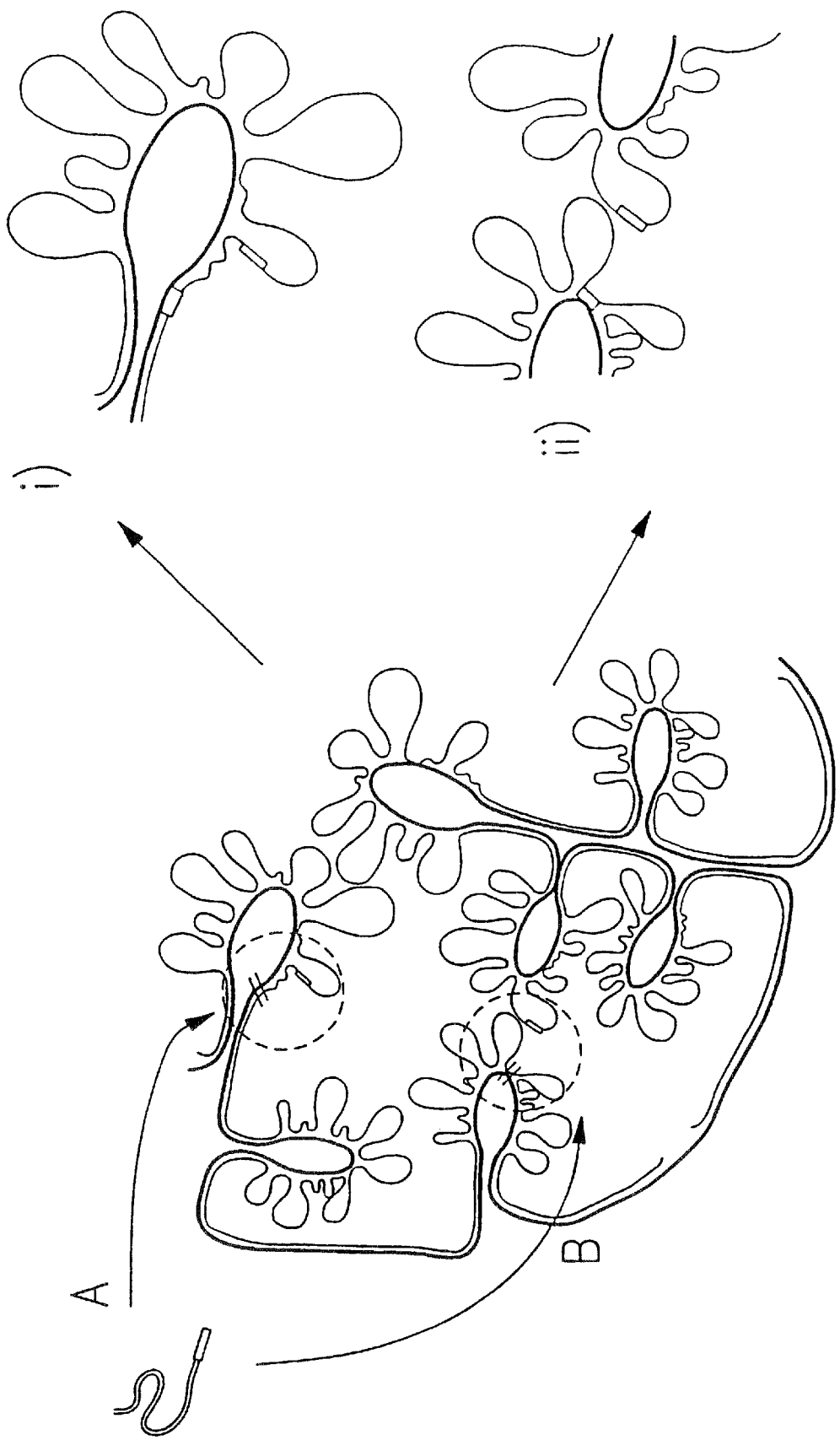
FIG. 6 illustrates a "Double Strand Break (DSB) Proximity" model of a RAM method in accordance with one embodiment of the present invention.

FIG. 6 illustrates a "Double Strand Break Proximity" model based on the ability of a double strand break (DSB) to enhance recombination in the local domain in which it has occurred. Heavy lines indicate the nuclear matrix/lamina and finer lines indicate chromosomal DNA. Note that the break in chromosomal DNA at the lamina delineates the end of one chromosome and the beginning of another. When a DSB (double slanted lines on chromatin loops) occurs the cell cycle arrests and the DNA at the site of the break becomes associated with DNA repair proteins which may reside on the nuclear matrix as "repair factories". This association alters the accessibility of the domain of chromatin in which the DSB has occurred (indicated by a circle of dashed lines) such that recombination over this domain is enhanced. An incoming linear DNA molecule can mimic a DSB and may therefore be targeted to repair factories at the nuclear matrix much like genomic DSB's. Accordingly, if linear recipient DNA (dark rectangle) is used by the cell to repair a genomic DSB in the same domain of accessibility as the target locus (white rectangle), one end invasion of the target locus and gene conversion would reconstruct a functional neo+ gene (FIG. 6A). Resolution of the event by unwinding would lead to two fluorescent spots adjacent to each other, the distance between them being within a local domain of chromatin accessibility of less than 2–3 Mb (i). Cross-over would lead to deletion of intervening sequences between the target locus and the site of integration of the recipient (with only one fluorescent spot for the recipient present). Alternately, far ectopic events would involve interaction of chromatin domains of two separate chromosomes (FIG. 6B). A linear recipient molecule used to repair a DSB on one chromosome would be able to interact with the target locus on a different chromosome if the domains containing the target locus and DSB are in close proximity to each other (most likely by association with the nuclear matrix). One end invasion and gene conversion at the target locus would lead to reconstruction of the neo+ gene. Release and unwinding of recipient would leave the target locus and chromosome unrearranged with the recipient integrating in the chromosome with the DSB (ii). Resolution by cross-over with the target locus would lead to translocation between the two chromosomes.

The present invention will be more readily understood by referring to the following examples which are given to illustrate the invention rather than to limit its scope.

EXAMPLE I

Ectopic Gene Targeting

Vector Construction and Preparation

Plasmid pA1059λTk (target) and pB115AdHyg (recipient) were derived from pMC1neopA (Stratagene). Briefly, 3' deletion of NgOmI/BamHI fragment or 5' deletion of EagI/NdeI fragment of the neomycin resistance gene, respectively, was followed by introduction of Not I restriction site in the NdeI or Aat II restriction site (to allow linearization of the vector). Next a herpes simplex virus thymidine kinase (HSV-tk) cassette (from pAGO) and a hygromycin (hyg) cassette (from p3'SS, Stratagene), respectively, were cloned into the multicloning site 3' of the truncated neomycin gene. Finally, 16 Kb λ virus sequence (GibcoBRL) or adeno viral sequence (GibcoBRL), lacking Not I restriction site, was cloned into the vectors between the the neomycin and HSV-tk or hygromycin cassette, respectively. Due to the large size of the vector, subsequent subcloning to prepare transfection quantities of DNA was carried out using SURE cells (Stratagene) and normal alkaline lysis miniprep followed by G-50 column was used to purify the DNA. Vector DNA was linearized by Not I and subjected to phenol chlorophorm extraction and ethanol precipitation before being resuspended in 1×TE for storage at −20° C.

Cell Culture and Transfection of LTA murine fibroblasts

LTA murine fibroblasts (Tk-, Aprt-) were cultured at 37° C., 5% $CO_2$ in complete medium (DMEM-F12 medium supplemented with 10% fetal bovine serum (FBS)). Cells were split the day before transfection and plated at either $5\times10^5$–$1\times10^6$ cells ($CaPO_4$) or at ~60% confluence (electroporation). Mother cells lines were produced by electroporation of LTA cells. Briefly, cells were trypsinized and concentrated by centrifugation, the cells were then resuspended in 1 ml of complete medium at room temperature. Upon counting, cells were diluted to 2.5 to $5\times10^6$ cells/ml with complete medium and 400 ul of cell suspension was electroporated (300 volts, 900 uF) using a gene Zapper 450/2500 apparatus (IBI) in the presence of 1–2 ug of target plasmid linearized at Not I. Cells were selected for integration of the plasmid in HAT medium. Positive clones were subcloned using glass cloning rings and expanded in culture for no more than 5 passages before being stored in liquid nitrogen. Genomic DNA was digested with restriction endonucleases and Southern analysis was carried out to determine the number of integrations. Cells exhibiting a simple hybridization pattern of integrated plasmid were then subjected to $CaPO_4$ transfection (Current Protocols, John Wiley Inc. USA, p. 9.1.4–9.1.9, 1996). Cells were fed 2 hours prior to transfection with 10 ml of fresh medium. Approximately 10 ug of DNA was coprecipitated with $CaPO_4$ and the precipitate was left on the cells for 4 hours followed by 3 min DMSO shock (10% DMSO in complete medium) or 16 hours without shock. Cells were washed with PBS twice and fed with 10 ml of complete medium. Thirty six hours after transfection 400 ug/ml of G418 (GibcoBRL) was added to the medium. G418 resistant colonies were picked as described for HAT resistance above. In addition, colonies were also subjected to hygromycin (GibcoBRL) at 250 ug/ml to determine resistance to the antibiotic.

Harvest of Cells for Fluorescent In situ Hybridization

LTA fibroblasts were grown to near 95% confluence before being trypsinized and replated at ½ to ¼ original confluence. Depending on the growth characterisitics of each clone, harvest of cells began at 20 to 22 hours after trypsinization by the addition of 2 drops of colchemid per 5 ml. Cells were incubated at 37° C., 5% $CO_2$ for 2 hours in the presence of coichemid, after which the cells were trypsinized and collected by centrifugation in 15 ml falcon tubes. Cells were then subjected to hypotonic shock by the addition of 10 ml of KCl (0.07 M, Sigma) for 20 minutes at 37° C. Cells were then centrifuged again before fixation in 10 ml of ice cold Carnoy I (3 part MeOH/1 part acetic acid). Fixation was repeated 3–4 times and cells were dropped on frozen slides (Fisher). Slides were cured for 24 hours at room temperature before being frozen at −20° C.

Southern Analysis

Genomic DNA was prepared as described above and digested with restriction endonucleases. Digested DNA was electrophoresed on 0.7% agarose gel (Agarose-NA, Pharmacia Biotech) and transferred to nylon membranes (Hybond N, Amersham). Hybridization was carried out with radiolabelled probe in 0.5 M sodium phosphate, pH 7.2, 7% SDS and 1 mM EDTA for 16–24 hours at 65° C. The blot was washed with several changes of 40 mM sodium phosphate, pH 7.2, 0.1% SDS at 65° C., and autoradiographed at −80° C. for 3 to 7 days.

Fluorescent In situ Hybridization

FISH analysis was carried out as previously described (Lemieux, N. et al., *Cytogenet. Cell Genet.* 59:311–312, 1994). Briefly, after Rnase treatment, chromosomes were denatured in 70% formamide in 2×SSC at 70° C. for 2.5 minutes. Hybridization was performed overnight at 37° C. in 50% formamide, 10% dextran 25 sulphate, 2×SSC, 0.1% sodium dodecyl sulphate, 1×denhardt (0.02% polyvinylpyrolidone, 0.02% Ficoll, 0.02% BSA, pH 7), and 1 mg/ml denatured sonicated salmon sperm DNA. Probes were denatured for 10 minutes at 95° C. in the same medium. Probe concentration was 4–5 ng/ul of dig-labeled adeno-2 viral DNA and/or 5–6ng/ul of biotin labeled λ virus DNA in a volume of 20 ul per slide. Rinses were performed at 37° C. for 2 minutes, twice in 50% formamide in 2×SSC followed by twice in 2×SSC. In addition high stringency washes were performed at 42° C. for 15 minutes once in 50% formamide in 2×SSC followed by a single 2×SSC rinse for 8 minutes at 37° C. Probes were generated from using the Bionick Labelling System (GibcoBRL) for biotin labeled probe or the Nick translation Kit (with addition of dig-11-dUTP, Boehringer Mannheim) for digoxigenin labelling.

Fluorescent Detection and Image Acquisition

After hybridization, the slides were incubated 45 minutes at 37° C. with rabbit antibiotin (Enzo), 4.6 ug/ml, in PBT (PBS: 0.2 N $NaH_2PO_4$, 0.2 $Na_2HPO_4$, 0.15 M NaCl pH 7.3, containing 0.15% BSA and 0.1% Tween 20). After 2 rinses in PBT at room temperature for 5 minutes, incubation was continued for 45 minutes in the presence of 10 ug/ml of biotinylated anti-rabbit goat antibody (GibcoBRL). Again after incubation slides were rinsed again as described before addition of fluorescein-streptavidin conjugate (GibcoBRL) at 8 ug/ml for final incubation of 45 minutes. During double detection the incubations continue with anti-dig mouse antibodies (1 ug/ml), anti-mouse-sheep Fab fragment (14 ug/ml) and anti-dig-sheep-rhodamine antibody (20 ug/ml) (Boehringer Mannheim). Counterstaining of DNA by propidium iodide (as described in Lemieux, N. et al., *Cytogenet. Cell Genet.* 59:311–312, 1994) or DAPI or was carried out before visualizing slides in presence of 10–15 ul of antifade solution. Antifade solution contained p-phenylene-diamine (PPD, Sigma, USA), 1 mg/ml of a mixture of glycerol:PBS 9:1 (v:v) adjusted to pH 9 with NaOH. Slides were visualized on a fluorescence microscope (Aristopan, Leitz) without a signal amplification system. Red, blue and green fluorescence was observed by viewing through a triple band-pass filter (Omega Optical Inc., Vermont, USA). Images were captured using a charge coupled device (CCD) camera (Xybion Electronic Systems) and MacProbe version 2.5 (PSI) on a Quadra 840av Macintosh™ computer. Color balance adjustments and file conversion were accomplished in Adobe Photoshop™ V2.5.1. Although images were captured electronically for publication, signals could be easily seen through the microscope and slide film was taken to attest this fact.

Results

One of the approaches of the present invention was to use ectopic gene targeting to analyse chromatin accessibility and DNA interaction in vivo. To do so, Fluorescent In Situ Hybridization (FISH) analysis was used to determine the integration pattern of an exogenous vector in three distinct cell lines each containing a target vector. These three cell lines were derived by electroporation of the murine fibroblast cell line LTA (tk- aprt-) with the target vector A1059λtk in a linear form (FIG. 1A). The target vector contains 16 kb of lambda sequence (used for FISH analysis) flanked by a 3' truncated neo gene (used for gene targeting) and a HSV-tk gene which was used for selection. Three tk+ cell lines were chosen and designated as A6 and A14, containing a single target vector, and A1 which contains two copies of the target vector (arranged head to tail). Each of the three lines was then subjected to $CaPO_4$ transfection with a recipient vector, B115Adhyg (FIG. 1A), containing a 5' truncated neo cassette with 600 bp of perfect homology with the 3' truncated neomycin gene of the target plasmid. As in the target vector the recipient vector contains unique sequences for FISH analysis (16 kb adeno-2 DNA) and a selection gene (hygromycin). Homologous recombination between the overlapping neo sequences in the two vectors will produce a functional neo gene which can be used for clonal selection in the presence of G418. The recipient vector was linearized via a Not I site, directly adjacent to the homology, to favor ectopic gene targeting events by leaving only one end of the recipient vector homologous to the target.

The usual gene targeting process involves invasion of the target by two homologous ends of the exogenous vector. Ectopic gene targeting involves invasion of the target sequence by only one homologous end of the exogenous vector, which then primes DNA synthesis leading to gene conversion (see FIG. 1B). At this point, there can be two outcomes. The recipient vector can form a homologous junction with the target at the target site while the other end of the recipient vector forms an illegitimate junction at or near the target site (FIG. 1B(i)). In this case the target site is modified. The other possibility is that the homologous end of the recipient vector is released and the recipient vector integrates elsewhere in the genome (FIG. 1B(ii)). In this case the target site is unchanged. Thus, by determining where the released recipient molecule integrates, one can determine what other areas (domains) of the genome were accessible to the target site at the time of the recombination event. This was accomplished by FISH analysis using probes specific for the target and recipient vector, which enabled the direct analysis of the distribution of integrated recipient DNA with respect to the target.

Characterization of Mother Clones A1, A6 and A14

Mother cell lines A1, A6 and A14 were subjected to Southern analysis to determine the copy number and structure of the integrated target sequences (see FIG. 2). By probing against the neomycin resistance gene, a diagnostic band(s) was produced for the target locus. Two diagnostic bands are apparent for A1 at 5.6 Kb (inter-vector band) and 8 Kb (junction band) indicating the integration of two target vectors in a head to tail configuration (A1 in FIGS. 2A and 3). A6 and A14 exhibit a single band of 5 kb and 3.8 Kb, respectively, which indicates a single integrated copy of the target for each cell line (A6 in FIGS. 2B and 3, A14 in FIGS. 2C and 3).

Figure 4A:
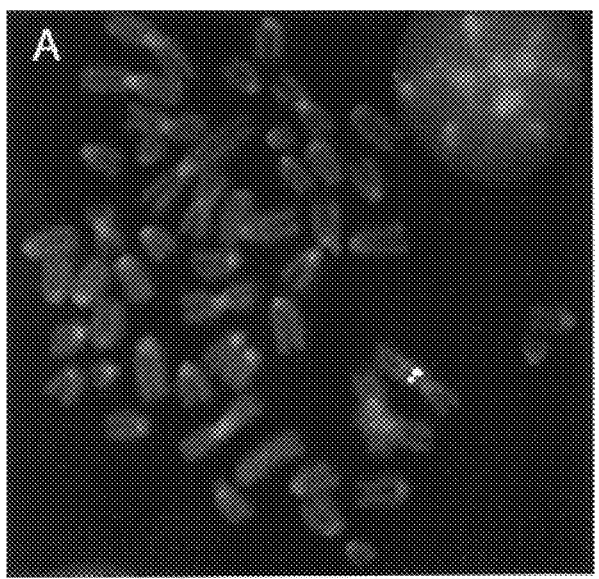
FIG. 4A to 4K illustrates Fluorescent In Situ Hybridization (FISH) analysis of clones obtained and isolated with a RAM method in accordance with one embodiment of the present invention.
Figure 4B:
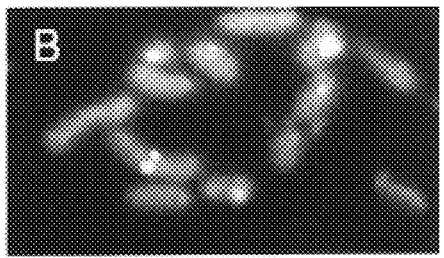
Figure 4C:
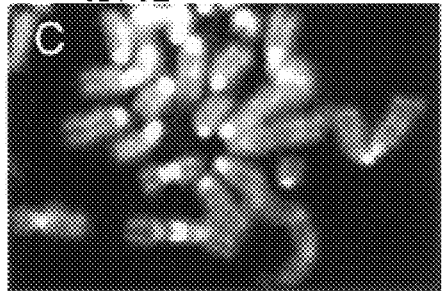
Figure 4D:
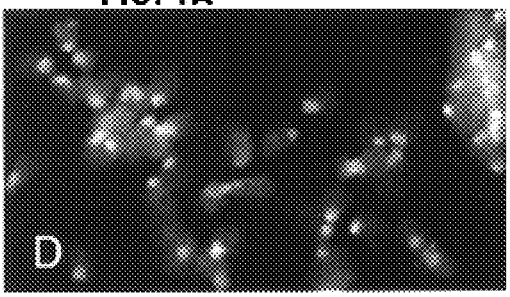
Figure 4E:
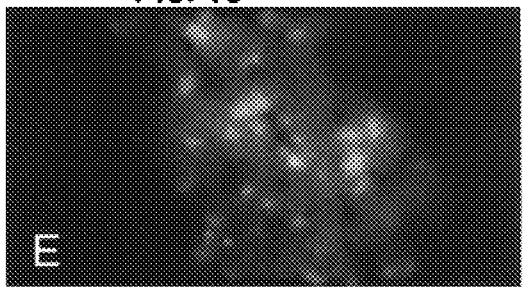
Figure 4F:
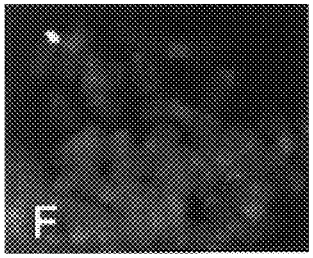
Figure 4G:
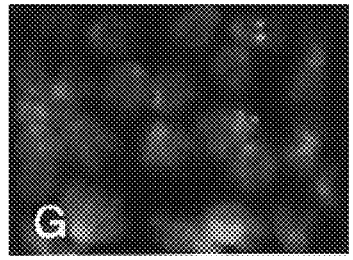
Figure 4H:
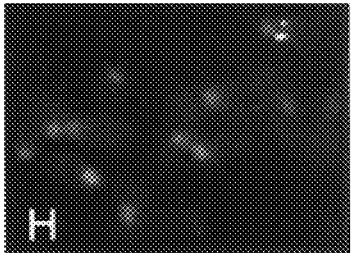
Figure 4I:
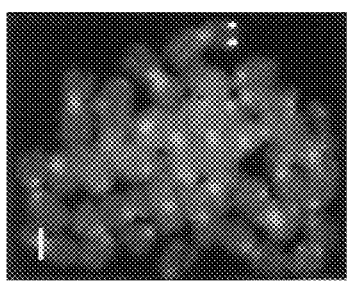
Figure 4J:
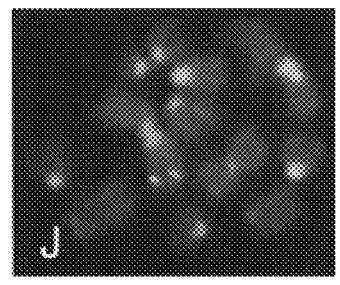

Mother cell lines A1, A6 and A14 were then subjected to single color FISH to determine the localization of the target vector. The location of the target locus in these cell lines is shown in FIG. 4. Clone A1, which has integrated 2 copies (arranged head to tail in tandem) of the target vector, contains the integrated sequences in a single site between the two centromeres of a dicentric chromosome (FIG. 4A). A6 contains a single integration of the target vector in the short satellite arm of an acrocentric chromosome (FIG. 4F) and A14 contains a single integration of the target vector in the mid arm of a large metacentric chromosome (FIG. 4I).

These cell lines were then transfected with the recipient vector. Selection for ectopic and illegitimate integration events was carried out in medium supplemented with G418 or hygromycin (respectively). Resistant clones were counted and homologous (ectopic gene targeting) and illegitimate integration frequencies were determined. Illegitimate integration in the three cell lines was similar exhibiting a mean frequency of $5.6 \times 10^{-3}$. Although A1 had twice the copy number of A6 or A14, homologous recombination rates for all three clones were quite similar with an average frequency of $2.0 \times 10^{-6}$. This agrees with previous reports that demonstrated that copy number does not affect homologous targeting frequencies significantly in mammalian cells.

Ectopic Gene Targeting Exhibits a Bimodal Distribution

Cell lines A1, A6 and A14 were transfected with the recipient vector and targeted events ($G418^R$ clones) were selected to be analysed by FISH. $G418^R$ clones were expanded with no more than 5 passages before cryopreservation and genomic DNA extraction. In the 5 daughter cell lines analyzed for A1 all but one (see FIG. 2A, A1.12) contained the 2 characteristic bands representing the target locus (i.e. 5.6 Kb and 8.0 kb band). The loss of the 5.6 Kb target band and an apparent shift of the 8.0 kb band, coupled with sensitivity to HAT medium (i.e. tk-) and FISH analysis (FIG. 4E) indicate that daughter clone A1.12 contains a crossover event. This event most likely involved the deletion of the 3' region beyond the neomycin resistance gene of the first integrated copy of the target vector along with the entire second copy of the target vector. Replacing these sequences is the 3' region of the recipient containing the adeno-2 viral DNA and hygromycin gene (see FIG. 3, A1.12). Consequently, both the lambda viral DNA and tk genes of both copies of the target have been deleted resulting in loss of the green fluorescent signal representing the target locus, which is replaced by the red of the recipient (FIG. 4E). It is more apparent in FIG. 2D that A1.12 contains a X-over event at the target locus, as the neo 1.1 kb band disappears and is replaced by a 1.3 kb band representing a full neomycin resistance gene (clones A1.2 and A1.5 which are ectopic events are 30 shown for comparison).

Figure 2A:
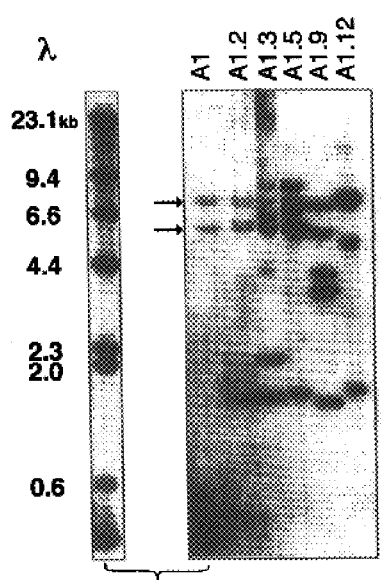
FIGS. 2A to 2D illustrate southern analysis of clones obtained and isolated with a RAM method in accordance with one embodiment of the present invention.

Overall, it is important to note that of greater than 30 $G418^R$ daughter clones analyzed by Southern for 5 different mother clones, only 2 were scored for the loss of the target locus. The four other daughter clones of A1 contain bona fide ectopic integrations (i.e.target locus is intact in each of them) Two of them, A1.2 and A1.5, have the recipient integrated in close proximity to the target (see FIGS. 4B and 4C, respectively) and retain the 2 characteristic target bands as shown in FIG. 2A. As well, in FIG. 2D the 1.1 kb band of target locus is present as expected for both A1.2 and A1.5. The two fluorescent signals can be resolved as two closely spaced but distinct spots at mitosis thus allowing for setting the limit on the distance between the target and recipient in these clones as being less than 2–3 Mb (Trask, B. J., *Trend. Genet.* 7:149–154, 1991). Clones A1.9 and A1.3, on the other hand, had integrated the recipient vector in a different chromosome than the target (mid arm of a small acrocentric chromosome (FIG. 4D); and mid arm of a metacentric chromosome, respectively.

Figure 2B:
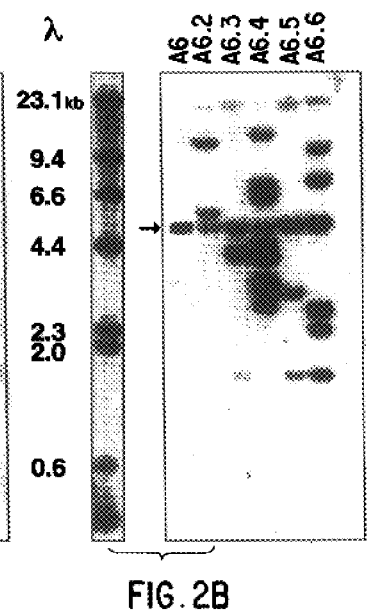
Figure 2C:
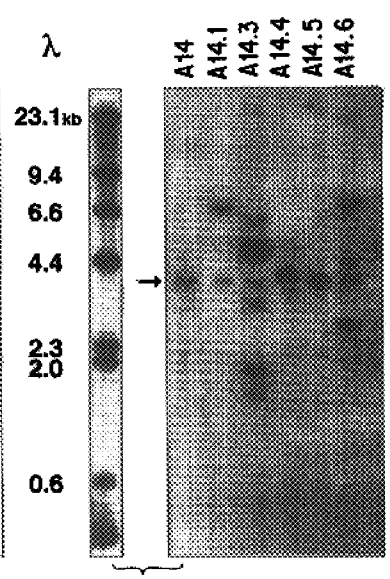
Figure 2D:
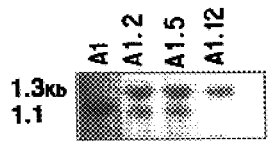
Figure 4K:
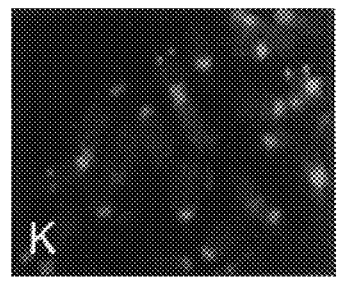

All 5 of the daughter clones derived from A6, in contrast, were the result of ectopic integration that occurred in different chromosomes than the target. A single band of 5.0 Kb representing the target locus is maintained in all 5 daughter clones indicating an intact target locus (FIG. 2B). Two daughter clones of A6, A6.2 and A6.3, are shown in FIGS. 4G and 4H (respectively). Daughter clones of A14 contain the single diagnostic band of 3.8 Kb, which indicates the target locus is intact in all 5 daughter clones. An intermediate distribution of ectopic events is seen with one clone exhibiting ectopic integration less than 2–3 Mb from the target, A14.4 (see FIG. 4J), and 4 others exhibiting integration of the recipient DNA molecule in other chromosomes than the one containing the target. The diagnostic band for the target locus is very intense and slightly shifted for A14.4. This shift was suggestive of a crossover event and Southern analysis using an alternate digestion (as in FIG. 2D) indicated that the target locus had been converted (appearance of 1.3 Kb band and loss of 1.1 kb band) yet FISH analysis indicated both target and recipient sequences were present (i.e. as separate spots at mitosis, approximately 2–3 Mb from each other; see FIG. 4J). A cross over would be expected to produce a single red spot as in A1.12 with loss of the green signal representing the target locus, or as an intermediate white color, which would indicate juxtaposed sequences of less than 100 Kb apart. Therefore, A14.4 most likely does not involve a crossover event and represents a rare ectopic event involving an as yet undefined mechanism. FIG. 4K shows colony A14.6, an example of one of the distant ectopic integration events with an apparent duplication of the target chromosome (most likely explained by non disjunction).

No insertion-type events were observed in our experiments. Such events were not likely since the recipient vector was linearized prior to transfection and only one end of the gene targeting vector is homologous to the target.

Thus, it appears that there are two distinct types of ectopic integration events. Those events which are in close proximity (<3 Mb) to the target (close) and those that occur in other chromosomes which do not contain the target locus (far). Integration of the recipient vector on the same chromosome at distances greater than 3 Mb from the target was not seen. This certainly does not imply that such events would not occur but it does indicate that such integration events would not be more likely than ones on distinct chromosomes.

Pooled FISH Analysis of Ectopic Gene Targeting Events

Pooled FISH analysis of an additional 24 $G418^R$ clones, 12 clones for A1, 6 clones for both A6 and A14 was carried out to discern trends in the preferences for certain chromosome morphologies for far integrations. In general, far ectopic integration events occurred in morphologically different chromosomes at multiple sites in the daughter clones of A1 and A14 mother cell lines, whereas A6 contains a large number of ectopic integrations in the mid arm of acrocentric chromosomes. A summary of all 39 clones analysed by FISH analysis, singularly or in pool, is shown in Table 1.

TABLE 1

Summary of G418[R] daughter clones analyzed by FISH

| | Total No. of Clones[b] | X over[c] | Same Chms | Diff. Chms | Acro Total | T | C | M | Meta Total | T | C | M |
|---|---|---|---|---|---|---|---|---|---|---|---|---|
| A1 | 17 | 2 | 14 | 3 | 1 | 0 | 0 | 1 | 2 | 1 | 0 | 1 |
| A6 | 11 | 0 | 1 | 10 | 7 | 0 | 0 | 7 | 3 | 1 | 1 | 1 |
| A14 | 11 | 1 | 2 | 9 | 7 | 1 | 2 | 4 | 2 | 1 | 0 | 1 |
| Totals | 39 | 3 | 17 | 22 | 15 | 0 | 2 | 5 | 7 | 1 | 1 | 2 |

[a]Includes all daughter clones analyzed by pool or independently.
[b]In the case of pooled clones: $10^5$ cells were pooled for each clone and the resulting pool of cells was passaged twice before harvest for FISH analysis. 100 mitosis were counted and scored for chromosome morphology and location of fluorescent signal (red) for recipient in relation to target locus (green). The resulting numbers of mitosis were converted to numbers of clones by dividing the number of each morphology type by 4.2, as on average one would expect to see 4.2 mitosis for each of the 24 clones in 100 mitosis.
[c]Cross-overs where scored when no target (green) fluorescent signal was present but had been replaced at the target locus by the recipient fluorescent signal (red)
Abbreviations: Acro = acrocentric; C = centromere; chms = chromosomes; Dicent = dicentric; N = mid arm; Neta = metacentric; T = telomere A1 daughter clones showed a striking number of close ectopic events within 2–3 Mb of the target (14 out of 17 clones), whereas A14 and A6 showed a much smaller number of close events (2 in 11 and 1 out of 11, respectively). Two of the close events for A1 were single cross-over events, and one event for A14 had an apparent cross-over coupled with ectopic integration, which brings the total number to 3 out of 39 clones (8%). In A6, 7 out of 11 clones (63.6%) were scored for the appearance of the recipient signal in the mid arm of an acrocentric chromosome. A14 did not show any bias for any one chromosome morphology or position and, due to the few number of far ectopic events, it was not possible to discern a trend for such events for A1. Although superficially it would appear A6 has a bias for acrocentric/mid arm localization of ectopic integration, it must be mentioned that there are 3 times more acrocentrics in the karyotype than metacentric and thus a frequency of ~64% does not indicate a statistically significant correlation for a specific chromosome morphology and position. What The analysis does indicate is that by using a pooling approach to FISH analysis one can produce a relatively large data set for analysing the distribution of ectopic gene targeting at a given locus. Our observations also lead us to suggest that far ectopic integrations can occur in more than one chromosome for a given locus. It remains to be determined if far events are random or if they occur in specific chromosomes.

The Distribution of Illegitimate Integration at Megabase Resolution is Stochastic The large number of close events in A1 vs. A6 or A14 raises a question of bias for integration in the dicentric chromosome. Southern or genetic analysis cannot indicate linkage over large distances on the same chromosome. Therefore, the distribution of illegitimate integration was analysed via FISH analysis since it gives a direct estimate of the distribution of illegitimate integration at megabase resolution.

Approximately 220 or 250 hygromycin resistant (HYG+) clones were pooled for cell lines A1 and A6, respectively, and subjected to two color FISH analysis. Approximately 3000 HYG+ clones were pooled for A14 to determine if the number of clones pooled for A1 and A6 could produce a representative distribution of illegitimate events. The distribution of illegitimate integration events in relation to the target locus was scored in 200 mitosis for relative position of the fluorescent signal on a chromosome (centromeric, telomeric or mid arm) as well as the morphology of the chromosome (acrocentric, dicentric or metacentric) containing the signal (see Table 2). The distribution of illegitimate events for all three clones was similar, indicating that illegitimate integration in these clones can not account for any differences in the pattern of ectopic gene targeting.

TABLE 2

Distribution of Illegitimate Integration without Ectopic Gene Targeting

| Clone (pool size) | No. of Mitosis (chms) | No. of Acro chms | No. of Meta chms | No. of Dicent chms | Mid arm | Telo | Centro | Signal In Same chms | Double Signal | Triple Signal |
|---|---|---|---|---|---|---|---|---|---|---|
| A1 (_220) | 200 (205) | 97 | 108 | 0 | 136 | 43 | 26 | 2 | 13 | 1 |
| A6 (_250) | 200 (212) | 134 | 76 | 2 | 154 | 30 | 26 | 0 | 13 | 0 |
| A14 (_3000) | 200 (207) | 119 | 80 | 8 | 132 | 40 | 27 | 3 | 12 | 0 |

TABLE 2-continued

Distribution of Illegitimate Integration without Ectopic Gene Targeting

| Clone (pool size) | No. of Mitosis (chms) | No. of Acro chms | No. of Meta chms | No. of Dicent chms | Mid arm | Telo | Centro | Signal In Same chms | Double Signal | Triple Signal |
|---|---|---|---|---|---|---|---|---|---|---|
| Total <%>[a] | 600 (624) | 350 <56.1> | 264 <42.3> | 10 <1.6> | 432 <69.2> | 113 <18.1> | 79 <12.7> | b <0.8>[b] | 38 b <6.3>[b] | b <0.2>[b] |

[a]Percentage of 624 chromosomes scored unless otherwise noted;
[b]Out of 600 mitosis scored
Abbreviations: Acro = acrocentric; Centro = centromere; chms = chromosomes; Meta = metacentric; Telo = telomere The distribution seen suggests that illegitimate integration in the presence of a chromosomal target is not biased, on a megabase scale, for any given chromosome or chromosomal position (i.e. telomere, centromere, mid arm) including the target chromosome and locus, respectively. The distribution reflects the prevalence of each chromosomal position and chromosome morphology. For example, there are ~18% telomeric signals on average and ~13% centromeric, or roughly two to one, and ~69% mid arm. This agrees well with the majority of chromosomal DNA being scored as mid arm and a count of one centromere and two telomeres per chromosome. All chromosome morphologies are represented roughly according to the proportion found in the karyotype. The karyotype is modal at a mean of 52 chromosomes and has on average 13 metacentric (or submetacentric), 37 acrocentric, 1 dicentric and 1 dot like chromosome (see FIG. 4A). Thus the chance of targeting any specific chromosome would be approximately 1 in 52 (~2%). Targeting the same 2 Mb unit of chromatin considering approximately 6000 such units in the average diploid mammalian genome would be 2 in 6000 (~0.03%). The chance of targeting an acrocentric is ~56% and for a metacentric is ~42% which is slightly skewed from the theoretical values of 71% and 25% (respectively) towards metacentrics. One explanation for this may be that metacentrics contain more DNA in general (see size difference in FIG. 4A) than acrocentrics. Considering that in normal murine karyotype all 40 chromosomes are acrocentric and similar in size it would follow that each metacentric (composed of essentially two acrocentric chromosomes after Robertsonian fusion) contains approximately twice the amount of DNA of a single acrocentric. Therefore each metacentric may provide more potential sites for integration to occur. In fact when considering this, one can create a theoretical karyotype of 65 chromosomes (i.e. 37 acrocentrics, 26 metacentric derived acrocentrics, one dicentric and one dot like chromosome). Using this karyotype the frequency for targeting a true acrocentric becomes ~57% and targeting a metacentric (i.e. actually two acrocentrics) is ~40%. These frequencies are very close to the actual observed frequencies in our analysis for transgene integration in acrocentric and metacentric chromosomes.

The dicentric chromosome was a target for illegitimate integration 1.6% of the time which agrees well with the theoretical value of 2%. Integration in the same chromosome as the target in about 1% of mitosis scored is noted. The majority of these were very close to the target and most likely targeted events as they appear at the same frequency as expected for ectopic gene targeting events.

Interestingly, two separate signals for the recipient vector were seen in ~6% of the 600 mitosis observed for the three pools. This would suggest that in a given transfection the incoming DNA will integrate in one locus in the majority of cells (>90%). The integrated DNA may be in tandem as well as physically separated by as much as 100 kb, as at interphase separate fluorescent signals could be discerned for loci which at metaphase appeared as a single intense spot. One triple signal was seen, but this was a rare event at 0.2%, and is most likely a double event coupled with non disjunction rather than three separate integrations. In toto, the data suggests that illegitimate integration in mammalian cells occurs primarily at a single site, stochastically, showing no bias for single chromosomes or chromosomal locations at megabase resolution.

Interphase Analysis of Far Ectopic Events

Interphase FISH analysis was conducted for 9 clones (2 derived from A1, 4 from A6 and 3 from A14) which contained far ectopic integration events on distinct chromosomes from the target. For each of the 9 clones distances between target (green) and recipient (red) sequences were measured to determine the frequency of co-localization of signals. Similar measurements were made for pools of clones containing illegitimate integrations of the recipient, derived from cell lines A1 and A6, to provide a random or "unlinked" distribution for co-localization of red and green signals. In addition, two clones from A1 and one clone from A14, containing close ectopic integrations, were used as a "linked" control for co-localization of FISH signals.

In a total of 247 nuclei observed for the 9 far ectopic clones, 35 nuclei (~14%) exhibited coincident or nearly coincident red and green signals. In contrast, a pool of ~440 clones containing random illegitimate integration events (unlinked loci) did not exhibit co-localization of red and green signals in 69 nuclei observed. The close (linked) control exhibited 63 coincident or nearly coincident FISH signals in all 63 nuclei observed. The distribution of inter signal distances for both the random (unlinked) control and the pool of far ectopic events approximated a normal distribution with the exception of a significant deviation ($p<0.0001$) for the number of co-localizations for the far ectopic events (see bin 0, FIG. 5). These results suggest that during interphase the site of integration of the recipient vector in far ectopic clones is found in close proximity to the target locus in a significant number of nuclei.

Discussion

Ectopic gene targeting exhibits a bimodal distribution in murine fibroblasts. The recipient DNA molecule may integrate nonrandomly within 3 Mb of the target or may integrate in other chromosomes, perhaps randomly. If indeed far events are random then integration in the target chromosome at distances beyond 3 Mb from the target locus may also occur. In our study, no far ectopic integrations where seen on the same chromosome as the target locus, nonetheless, such events cannot statistically be excluded. A bimodal distribution was observed for 39 ectopic gene targeting events analysed for 3 independent target loci (either separately or in pools). In contrast, illegitimate integration of the recipient vector was shown to be random at the resolution of our FISH analysis. Our experiments were carried out on unsynchronized cell populations such that the effects of the cell cycle can not be addressed directly. Neverthless, the results were highly reproducible between independent experiments.

The results obtained in accordance with the present invention, lead us to suggest a model for genomic domain interactions that takes into account the observed bimodal distribution of ectopic gene targeting. FISH analysis of the integration pattern of illegitimate events indicates that at a resolution of 10–20 Mb there is no evident bias with respect to chromosomal location. In other words, integration appears random. This is the case despite the presence of the homologous genomic target. Thus, it appears that homology per se does not act as a determining factor in the localization of the integration site. Yet when a double strand break is introduced in genomic homologous sequences, integration occurs highly preferentially at the site of the break by homologous recombination (Rouet, P. et al., *Mol. Cel. Biol.* 14:8096–8106, 1994). From these observation it would seem that the location of the integration site is first and foremost determined by the occurrence of a double strand break in genomic DNA and that if this DSB occurs at or near homologous sequences then the integration will most likely involve homologous recombination.

If natural DSBs occur randomly in the genome, then a DSB in any given 2 megabase unit should occur at a frequency of about $3.3 \times 10^{-4}$ considering there are $6 \times 10^9$ bases in the diploid murine genome. Since the overall frequency of illegitimate recombination for our cell lines is $6 \times 10^{-3}$ then the frequency of integration at a DSB within a 2 megabase domain containing the target should be the product of the two ($3.3 \times 10^{-4}$ multiplied by $6 \times 10^{-3}$), thus $2 \times 10^{-6}$. Interestingly, this is the frequency at which ectopic gene targeting is noted which is also similar to the frequency of traditional gene targeting. This similarity in frequencies has been observed previously by other groups. These frequencies are in agreement with integration involving first a DSB break which, if it occurs at or near a homologous target, will result in gene targeting. Thus, this could explain the ectopic gene targeting events that occur in close proximity to the target. According to the above reasoning, this would mean that the DSB occurred in a domain that, although situated in a distinct chromosome, was in close proximity to the domain containing the homologous target at the time of the ectopic gene targeting event. In support of a close association of far ectopic sites to the target locus at the time of recombination, a significant number of co-localizing recipient and target signals were observed by FISH in interphase nuclei of 9 separate far ectopic clones produced from mother clones A1, A6 and A14. In contrast, no co-localizations were observed for pools of random illegitimate events which exhibited a normal distribution of inter signal distances between recipient and target sequences at interphase. It is tantalizing to speculate that such domain associations may be occurring in a cell cycle specific manner linked with either replication or transcription. A "Double Strand Break Proximity" model, presented in FIG. 6, summarizes this hypothesis.

An obvious alternative to this model would be to invoke that gene conversion between the target and the exogenous vector occurs first, followed by release of the vector and random integration in the genome via illegitimate recombination. The frequencies for each of these events do not support this hypothesis. Gene conversion between an exogenous vector and a genomic homologous target has been measured and were found to be $<10^{-6}$. Since the frequency of illegitimate integration in our assay is $6 \times 10^{-3}$, then the frequency of ectopic gene targeting, if it occurred in these two successive steps, should be the product of the frequencies of each step or $10^{-8}$ to $10^{-9}$. This is at least two orders of magnitude lower than what is seen for the frequency of ectopic gene targeting. Of course it may be that, after the gene conversion step, the exogenous vector becomes highly potentiated for integration. Taking this possibility into account, still the site of integration should be near the target site as depicted in FIG. 5, to explain the observed bimodal distribution which is therefore not random.

In support for the concept that integration is driven by a DSB, It has been observed that illegitimate integration of an exogenous vector occurs at only one site, greater than 90% of the time (Folger, K. R. et al., *Mol. Cell. Biol.* 2:1372–1387, 1982; Richard, M. et al., *Mol. Cell. Biol.* 14:6689–6695, 1994). Furthermore, when there is a gene targeting event, rarely is there also in the same cell a separate illegitimate integration event even though the later occurs usually a thousand times more frequently than the former. Thus, this suggests that in most of the cells where an integration event (homologous or illegitimate) occurs, there is only one genomic site available for integration. Recently, it has been shown that as few as one double strand break can cause p53-dependent cell cycle arrest in human embryonic fibroblasts (Huang, L. C. et al., *Proc. Natl. Acad. Sci. USA* 93:4827–4832, 1996). CaPO$_4$ treatment of cells alone can also induce p53 cell cycle arrest (Renzing, J., et al., *Oncogene* 10:1865–1868, 1995). Cell cycle arrest triggered by CaPO$_4$ and/or DNA damage may therefore provide a means of limiting the number of DSBs that can accumulate during a given cell cycle, thus limiting the potential number of sites of integration of exogenous DNA.

The number and types of close (targeted or 5 crossover) events and far ectopic gene targeting events were distinct for all three loci. These trends were even more evident upon pooled analysis of an additional 24 G418$^R$ clones from A1 (12 clones), A6 (6 clones) and A14 (6 clones). Clone A1 had the highest number of close events and the least far ectopic integrations, followed by A14 and then A6 (with the most far events and only one close event). Only clone A6 showed a strong preference for a specific chromosome location and morphology, where ~64% of ectopic integrations occurred in the mid arm of acrocentric chromosomes. A1 and A14 showed weaker trends for specific chromosomes but this may only be due to the reduced number of distant ectopic integrations seen for these clones.

Since the distribution of close and far events differs between loci this suggests a site specific effect on ectopic gene targeting.

It is apparent that chromatin within the nucleus is organized in a coherent manner such that gene sequences may be accessed at certain points in the cell cycle for replication and transcription.

Compartmentalization seems to occur for these processes (ex. transcription factories (Cook, P. R., *J.Cell Sci.* 108:2927–2935, 1995); replication factories (Jackson, D. A., *Bioessays* 17:587–591, 1990)), the factors they require (ex. splicing factors (Spector, D.L. et al., *Cold Spring Harbor Symp. Quant. Biol.* 58:799–805, 1993)) and the chromatin involved (chromosome territories (Cremer T. et al., *Cold*

*Spring Harbor Symp. Quant. Biol.* 58:777–792, 1993)). The transcription and replication factories may be able to organize DNA domains from the same chromosome or from distinct chromosomes in such a way that accessibility of one domain to another may be enhanced. Using this line of reasoning, it may not be at all surprising that domains on distinct chromosomes have access to each other.

Ectopic gene conversion occurs naturally among non allelic sequences in many organisms and the mechanism of ectopic gene targeting also seems to be conserved across phila. In the present Application, it has been demonstrated that ectopic gene targeting exhibits a bimodal distribution of integration in murine cells. This indicates that both intra and interchromosomal sites are accessible to the targeting vector. Thus, the RAM method in accordance with the present invention may by used to analyse ectopic gene targeting and to determine which chromosomal domains within the genome are accessible to a given genetic locus.

What is claimed is:

1. A method for identifying within a living cell, two chromosomal regions positioned during interphase in three-dimensional physical proximity one with another, comprising the steps of:

a) providing a linear DNA vector having a first end and a second end, the first end of said vector comprising a nucleotide sequence homologous to a first region of a chromosome and being capable of homologous recombination thereto, said first chromosomal region comprising a known non-repetitive DNA sequence, the second end of said vector comprising a nucleotide sequence non-homologous to the chromosomes of said cell, said second end being capable of illegitimate integration with a second region of a chromosome in physical proximity to said first chromosomal region;

b) introducing said DNA vector into said cell;

c) allowing said first end of said vector to recombine with said first chromosomal region and said second end to illegitimately integrate with said second chromosomal region; and d) detecting said homologous recombination event and said second chromosomal region whereupon said second end of said vector illegitimately integrated, thereby identifying said two physically proximal chromosomal regions.

2. The method of claim 1, wherein said known non-repetitive DNA sequence is unique within said cell.

3. The method of claim 1, wherein the second end of said DNA vector illegitimately integrates into a DNA double strand break of a chromosome.

4. The method of claim 1, wherein said DNA vector further comprises, at each one of said ends, at least one detection element selected from the group consisting of a tag, a label, a signal, a polymerase chain reaction (PCR) primer sequence, a reporter gene and a portion of a reporter gene.

5. The method of claim 4, wherein said DNA vector comprises at least one signal selected from the group consisting of fluorescence in situ hybridization signals (FISH), radioactive in situ hybridization signals, confocal microscopy in situ hybridization signals and electron microscopy in situ hybridization signals, said at least one signal allowing for detection of in situ hybridization of said DNA vector.

6. The method of claim 1, wherein said first region of a chromosome is modified to introduce a first part of a reporter gene, and wherein said vector comprises a second part of the reporter gene, such that recombination of the first end of said vector with said first chromosomal region and illegitimate integration of said second end with said second chromosomal region allows the reporter gene to be functional.

7. The method of claim 6, wherein said second part of the reporter gene is localized between said first and second ends of said DNA vector.

8. The method of claim 6, wherein said reporter gene is a selection gene.

9. The method of claim 8, wherein said selection gene is selected from the group consisting of neomycin, puromycin, hygromycin, and herpes simplex thymidine kinase.

10. The method of claim 1, wherein the first end of said vector is at least 300 bp in length.

11. The method of claim 1, wherein the first end of said vector is at least 500 bp in length.

12. The method of claim 1, wherein the first end of said vector is at least 700 bp in length.

13. The method of claim 1, wherein the second end of said vector is at least 1 Kb in length.

14. The method of claim 1, wherein the second end of said vector is at least 10 Kb in length.

15. The method of claim 1, further comprising the step of determining the DNA sequence of at least a portion of said second chromosomal region.

16. The method of claim 1, wherein about 1–2 $\mu$g of the DNA vector is transfected into said cell using an electroporation method.

17. The method of claim 1, wherein said cell is a mammalian cell.

18. The method of claim 1, wherein said physical proximity of said first and second chromosomal regions is indicative that said regions contain functionally related genes or a regulatory element functionally related to said known non-repetitive DNA sequence.

19. A method for locating in chromosomes of a living cell, a DNA double strand break positioned during interphase in three-dimensional physical proximity with a known non-repetitive DNA sequence, comprising the steps of:

a) providing a linear DNA vector having a first end and a second end, the first end of said vector comprising a nucleotide sequence homologous to a first region of a chromosome comprising a known non-repetitive DNA sequence and being capable of homologous recombination thereto, the second end of said vector comprising a nucleotide sequence non-homologous to the chromosomes of said cell, said second end being capable of illegitimate integration into a DNA double strand break of a chromosome in physical proximity to said first chromosomal region;

b) introducing said DNA vector into said cell;

c) allowing said first end of said vector to recombine with said first chromosomal region and said second end to illegitimately integrate into said DNA double strand break; and d) detecting said homologous recombination event and said DNA double strand break whereupon said second end of said vector illegitimately integrated, thereby locating said DNA double strand physically proximal with said known non-repetitive DNA sequence.

20. The method of claim 1, wherein the first and the second chromosomal regions are on the same chromosome and are separated by a distance smaller than about 3 Mb.

21. The method of claim 1, wherein the first and the second chromosomal regions are on two distinct chromosomes.

* * * * *